United States Patent [19]

Staendeke et al.

[11] 4,092,363
[45] May 30, 1978

[54] PRODUCTION OF DIALKYLPHOSPHINE OXIDES

[75] Inventors: Horst Staendeke, Bruhl; Hubert Neumaier, Hurth, both of Germany

[73] Assignee: Hoechst Aktiengesellschaft, Frankfurt am Main, Germany

[21] Appl. No.: 728,234

[22] Filed: Sep. 30, 1976

[30] Foreign Application Priority Data

Oct. 6, 1975  Germany .............................. 2544606

[51] Int. Cl.$^2$ ................................................ C07F 9/53
[52] U.S. Cl. ............................................ 260/606.5 P
[58] Field of Search ................................. 260/606.5 P

[56] References Cited

U.S. PATENT DOCUMENTS

| 3,126,416 | 3/1964 | Willans ........................ 260/606.5 P |
| 3,855,311 | 12/1974 | Staendeke .................... 260/606.5 P |

FOREIGN PATENT DOCUMENTS

| 1,568,928 | 4/1970 | Germany ....................... 260/606.5 P |
| 1,952,605 | 2/1972 | Germany ....................... 260/606.5 P |

*Primary Examiner*—Helen M. S. Sneed
*Attorney, Agent, or Firm*—Connolly and Hutz

[57] ABSTRACT

Production of dialkylphosphine oxides of the general formula:

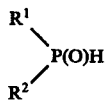

in which $R^1$ and $R^2$ each stand for an alkyl group having from 1 to 4 carbon atoms by subjecting a dialkylchlorophosphine of the general formula:

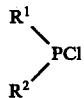

in which $R^1$ and $R^2$ have the meanings given above, or an addition product thereof with hydrogen chloride, to alcoholysis with an aliphatic $C_1 - C_4$ alcohol in the presence of a protective gas at temperatures between $-30°$ and $+30°$ C, and subjecting the resulting alcoholysate to thermolysis. The compounds are more specifically produced by continuously adding the dialkylchlorophosphine component to the alcohol; subjecting the resulting alcoholysate to thermolysis in a heated separation zone; introducing into the separation zone, countercurrently to the alcoholysate, 10 to 150 l/h of a protective gas, per liter of alcoholysate; removing simultaneously from the separation zone the gaseous thermolysis products and, separately from said products, an alcoholic solutions containing desirable final product; neutralizing the alcoholic solution and recovering the final product from said solution in known manner.

7 Claims, 1 Drawing Figure

U. S. Patent May 30, 1978 4,092,363
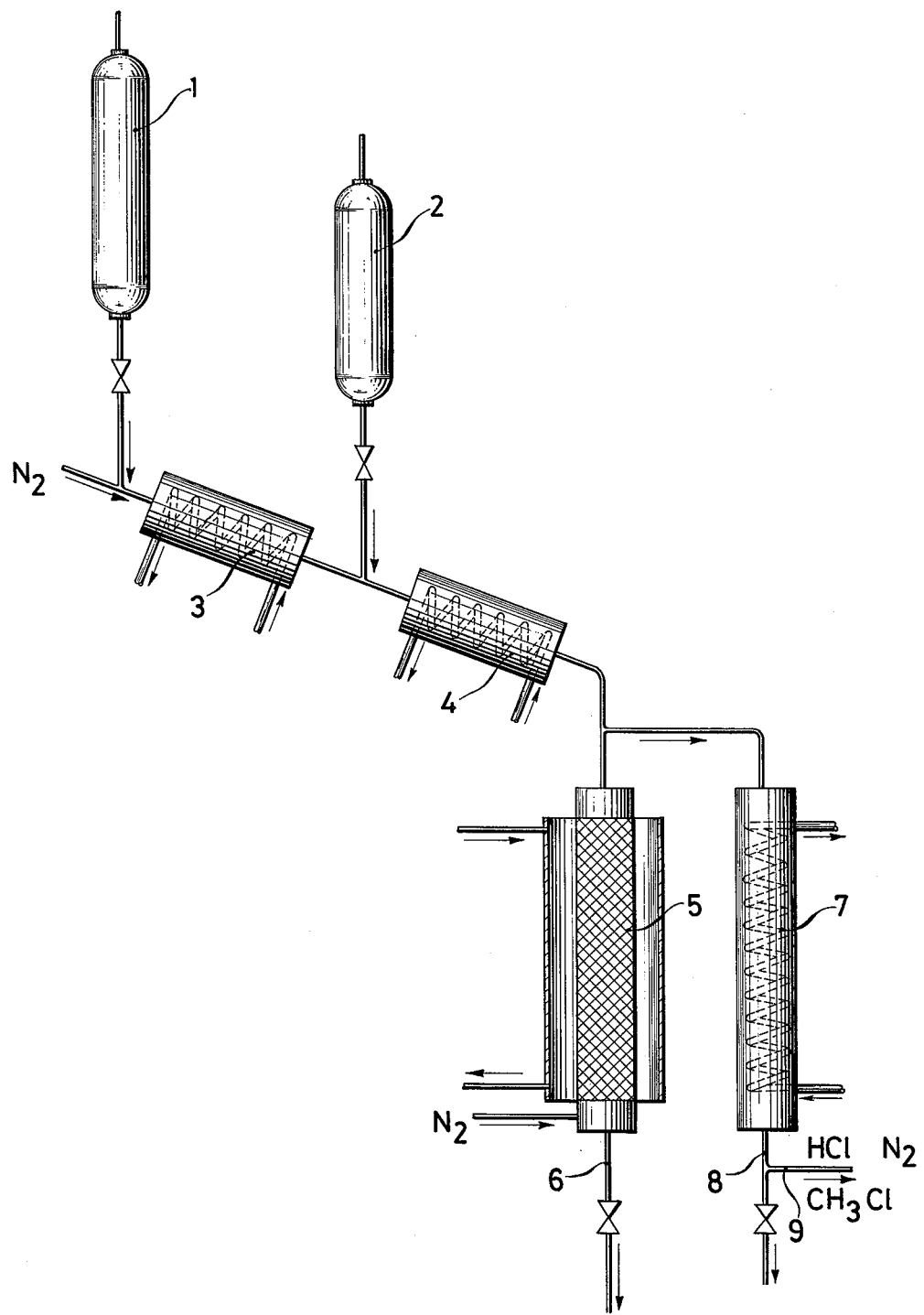

PRODUCTION OF DIALKYLPHOSPHINE OXIDES

This invention relates to a process for making dialkylphosphine oxides of the general formula:

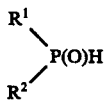

in which $R^1$ and $R^2$ each stand for an alkyl group having from 1 to 4 carbon atoms by subjecting a dialkylchlorophosphine of the general formula:

in which $R^1$ and $R^2$ have the meanings given above, or an addition product thereof with hydrogen chloride, to alcoholysis with an aliphatic $C_1 - C_4$ - alcohol in the presence of a protective gas at temperatures between $-30°$ and $+30°$ C, and subjecting the resulting alcoholysate to thermolysis.

It has been described (cf. German Patent Specification No. 1 952 605) that dialkylphosphine oxides can be made by subjecting a dialkylchlorophosphine or an addition product thereof with hydrogen chloride to alcoholysis.

This reaction is carried out at temperatures between $-70°$ and $+70°$ C under a protective gas. More specifically, the dialkylchlorophosphines or their addition products with hydrogen chloride are slowly added dropwise with thorough agitation to the alcohols. Once the neutralization has been terminated, the alcohol is extensively distilled off and water, which is in the residue, is removed by subjecting the benzene/water-mixture to azeotropic distillation. After separation of the neutralization salts, the filtrate is distillatively freed from benzene, and crude phosphine oxide is obtained as the residue.

This process suffers from the disadvantage that the dialkylchlorophosphine may well undergo further reaction with formed dialkylphosphine oxide in accordance with the following reaction equation

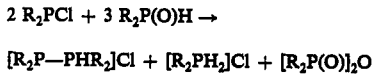

with the resultant formation of undesirable by-products (cf. F. Seel et al., Chem.Ber. 104, 2972 (1971)).

Further disadvantages reside 1. in the need to heat the whole reaction mixture for some prolonged time to effect thermal decomposition of intermediary dialkylalkoxyphosphonium chloride

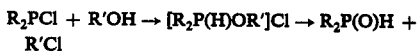

which means that the sensitive dialkylphosphine oxides are subjected to unnecessary thermal stress, and 2. in the fact that the process, which is carried out discontinuously, is difficult to effect on an industrial scale.

In accordance with our present invention, we have unexpectedly found that the process described in German Patent Specification No. 1 952 605 can be improved and carried out continuously, the improved process comprising: continuously adding the dialkylchlorophosphine component to the alcohol; subjecting the resulting alcoholysate to thermolysis in a heated separation zone; introducing into the separation zone, countercurrently to the alcoholysate, 10 to 150 l/h of a protective gas, per liter of alcoholysate; removing simultaneously from the separation zone the gaseous thermolysis products and, separately from said products, an alcoholic solution containing desirable final product; neutralizing the alcoholic solution and recovering the final product from said solution in known manner.

The alcoholysate is preferably subjected to thermolysis at temperatures of 60° to 120° C, more preferably 80° to 100° C.

It is also preferable to introduce 10 to 60 liter/h of protective gas, per liter of alcoholysate, into the separating zone, nitrogen and/or hydrogen chloride being most preferably used as the protective gas. The dialkylchlorophosphine components which are most preferably used in this invention are selected from the crude products containing dialkylchlorophosphines and/or their addition products with hydrogen chloride, obtained by one of the processes described in German Patent Specification No. 1 568 928 and U.S. Pat. Nos. 3,607,934 and 3,855,311.

It is finally preferable in accordance with this invention first to dissipate the reaction heat set free on effecting the alcoholysis by conveying the alcoholysate through at least one heat exchanger zone, and to introduce the alcoholysate leaving the heat exchanger zone into the separating zone.

The dialkylchlorophosphines which are useful in the process of this invention comprise, for example: dimethylchlorophosphine, diethylchlorophosphine, dipropylchlorophosphine, and dibutylchlorophosphine as well as mixed dialkylchlorophosphines, such as methylethylchlorophosphine, ethylbutylchlorophosphine and their addition products with hydrogen chloride.

The alcohols which it is preferable to use comprise aliphatic alcohols having from 1 to 4 carbon atoms, the most preferred alcohol being methanol. The alcohol is more advantageously used in at least three times the quantity stoichiometrically necessary.

With respect to the intermediary phosphonium chloride, it is absolutely necessary for it to be subjected to thermolysis, prior to effecting its transformation to dialkylphosphine oxide. This has been evidenced by tests, wherein the alcoholysate was directly neutralized with ammonia with the resultant unexpected formation of only trialkylphosphine oxide. In other words, the product obviously underwent complete isomerization under these conditions, in accordance with the following schematic equation.

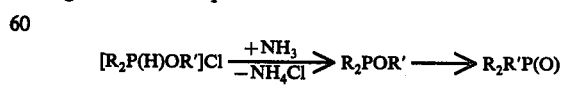

and in accordance with the literature (cf. F. Seel et al., Chem.Ber. 105, 406 (1972)).

Dialkylphosphine oxides are important intermediates for making surfactants, flame-retardant agents for various plastics, and biocides.

In addition to this, dimethylphosphine oxide which is the lowest dialkylphosphine oxide representative, possesses bacteriostatic and bactericidal properties.

EXAMPLE 1

An apparatus such as that shown diagrammatically in the accompanying drawing was used. 600 g (18.7 mol) of methanol coming from a reservoir 1 was passed within 2.5 hours through a cooler 3, mixed under nitrogen, which was supplied at a rate of 10 l per hour, with 155 g (1.61 l mol) of dimethylchlorophosphine coming from a second reservoir 2, and the resulting mixture was cooled in a further cooler 4. The coolers 3 and 4 were both maintained at a temperature of −30° C. The reaction mixture was delivered to the head of a separating column 5 which was heated to 100° C by means of steam and packed with Raschig rings 6 mm wide. Nitrogen was introduced into the base portion of the column 5 at a rate of 10 l per hour which caused the methyl chloride formed by thermolysis to distil over together with a portion of the methanol in excess into a condenser 7. 488 g (15.2 mol) of condensed methanol, which had a purity of 99.5%, determined by gas-chromatography, was removed from the condenser 7 through a conduit 8, and uncondensed matter, such as HCl, $N_2$ and $CH_3Cl$, was removed through a branch conduit 9. At the same time, base product, which was a methanolic solution of dimethylphosphine oxide, was taken from a separating column 5 through a conduit 6, and collected. The solution was subjected to gas-chromatographical analysis and found to contain 81 g (1.04 l mol or 65% of the therotical) of dimethylphosphine oxide. The crude product was converted to pure crystalline material in the manner described in German Patent Specification No. 1 952 605.

EXAMPLE 2

510 g (15.9 mol) of methanol was reacted with 137 g (1.42 mol) of dimethylchlorophosphine in the manner described in Example 1. Prior to the reaction, the dimethylchlorophosphine had been saturated with hydrogen chloride gas while cooling.

The base product was subjected to gas-chromatographical analysis and found to contain 85 g (1.09 mol or 77% of the theoretical) of dimethylphosphine oxide. 364 g (11.4 mol) of methanol was obtained as the distillate.

EXAMPLE 3

570 g (17.8 mol) of methanol was reacted with 144 g (1.49 mol) of dimethylchlorophosphine in the manner described in Example 1, but hydrogen chloride, which replaced the nitrogen, was introduced into the column base at a rate of 20 l per hour.

The base product was subjected to gas-chromatographical analysis and found to contain 106 g (1.36 mol) or 91% of the theoretical) of dimethylphosphine oxide. 310 g (9.7 mol) of methanol was recovered as the distillate.

EXAMPLES 4 to 10

Various experiments were made in the manner described in Example 1 on a crude phosphine mixture, which was obtained by the process described in German Patent Specification No. 2 255 395 and had the following composition, determined by NMR-analysis:
39% of $(CH_3)_2PCl$; 5% of $CH_3PCl_2$; 8% of $(CH_3)_2PH$; 48% of HCl.

The following quantities of nitrogen were introduced into the base portion of the separating column, which replaced the 10 l per hour supply of nitrogen, in Example 1.

| Exp. No. | Quantity of crude phosphine (g) | Quantity of nitrogen (l per h) | $(CH_3)_2P(O)H$-yield (% of the theoretical) |
|---|---|---|---|
| 4 | 201 | 0 | 61 |
| 5 | 200 | 5 | 80 |
| 6 | 201 | 10 | 93 |
| 7 | 200 | 20 | 86 |
| 8 | 202 | 30 | 82 |
| 9 | 201 | 60 | 75 |
| 10 | 199 | 100 | 59 |

EXAMPLES 11 TO 14 (Comparative Examples)

A series of experiments was made in the manner described in Example 1 of German Patent Specification No. 1 952 605 on the same crude phosphine mixture as that used in Examples 4 to 10.

To this end, about 150 g of the mixture was dropped within about 2 hours under nitrogen and at −15° C into 1 liter of methanol. After the reaction was terminated, the reaction product was heated for various periods to 70° C, allowed to cool and neutralized by means of ammonia. After separation of ammonium chloride, the filtrate was subjected to gas chromatographical analysis.

| Exp. No. | Quantity of crude phosphine (g) | Heating period at 70° C (h) | $(CH_3)_2P(O)H$-yield (% of the theoretical) |
|---|---|---|---|
| 11 | 188 | 1 | 82 |
| 12 | 148 | 3 | 75 |
| 13 | 144 | 6 | 74 |
| 14 | 140 | 12 | 73 |

We claim:
1. In a process for making dialkylphosphine oxides of the general formula:

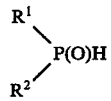

in which $R^1$ and $R^2$ each stand for an alkyl group having from 1 to 4 carbon atoms by subjecting a dialkylchlorophosphine of the general formula:

in which $R^1$ and $R^2$ have the meanings given above, an addition product thereof with hydrogen chloride or mixture thereof, to alcoholysis with an aliphatic $C_1$–$C_4$ alcohol in the presence of a protective gas at temperatures between −30° and +30° C, and subjecting the resulting alcoholysate to thermolysis, the improvement which comprises:
continuously adding the dialkylchlorophosphine component to the alcohol; subjecting the resulting alcoholysate to thermolysis in a heated separation zone; introducing into the separation zone, countercurrently to the alcoholysate, 10 to 150 l/h of a protective gas, per liter of alcoholysate; removing simultaneously from the separation zone the gaseous thermolysis products and, separately from said products, an alcoholic solution containing desirable final product; neutralizing the alcoholic solution and recovering the final product from said solution.

2. The process as claimed in claim 1, wherein the alcoholysate is subjected to thermolysis at temperatures of 60° to 120° C.

3. The process as claimed in claim 2, wherein the thermolysis is effected at 80° to 100° C.

4. The process as claimed in claim 1, wherein nitrogen or hydrogen chloride or both are introduced into the separating zone as protective gas.

5. The process as claimed in claim 1, wherein 10 to 60 l per hour of protective gas is introduced, per liter of alcoholysate, into the separating zone.

6. The process as claimed in claim 1, wherein the reaction heat set free on effecting the alcoholysis is dissipated by conveying the alcoholysate through at least one heat exchanger zone and the alcoholysate leaving the heat exchanger zone is introduced into the separating zone.

7. The process as claimed in claim 1, wherein the dialkylchlorophosphine, an addition product thereof with hydrogen chloride or mixture thereof is the crude product produced by the process comprising reacting vaporous phosphorus with an alkyl chloride in the presence of active carbon as catalyst.

* * * * *